United States Patent [19]

Alexander

[11] Patent Number: 5,785,662
[45] Date of Patent: Jul. 28, 1998

[54] BLOOD COLLECTION ASSEMBLY WITH PLURALITY OF VIALS

[75] Inventor: Gary E. Alexander, Baton Rouge, La.

[73] Assignee: Medisys Technologies, Inc., Baton Rouge, La.

[21] Appl. No.: 656,848

[22] Filed: May 30, 1996

[51] Int. Cl.$^6$ .................................................. A61B 5/00
[52] U.S. Cl. .................................................. 600/575
[58] Field of Search ........................ 128/760, 762, 128/770; 604/403, 407, 411

[56] References Cited

U.S. PATENT DOCUMENTS

| | | | |
|---|---|---|---|
| 3,765,402 | 10/1973 | Grabhorn | 128/762 |
| 4,026,287 | 5/1977 | Haller | 128/215 |
| 4,197,846 | 4/1980 | Bucalo | 128/218 |
| 4,425,120 | 1/1984 | Sampson et al. | 604/198 |
| 4,581,021 | 4/1986 | Landau et al. | 604/212 |
| 4,636,202 | 1/1987 | Lowin et al. | 604/236 |
| 4,702,738 | 10/1987 | Spencer | 604/198 |
| 4,784,157 | 11/1988 | Hells et al. | 128/762 |
| 4,875,895 | 10/1989 | Kurtz | 604/187 |
| 4,883,472 | 11/1989 | Michel | 604/208 |
| 4,894,055 | 1/1990 | Sudnak | 604/198 |
| 4,936,830 | 6/1990 | Verlier | 604/110 |
| 4,944,723 | 7/1990 | Haber et al. | 604/110 |
| 4,966,592 | 10/1990 | Burns et al. | 604/198 |
| 4,973,316 | 11/1990 | Dysarz | 604/195 |
| 4,973,317 | 11/1990 | Bobrove | 604/198 |
| 4,976,701 | 12/1990 | Ejlersen et al. | 604/192 |
| 4,986,819 | 1/1991 | Sobel | 604/198 |
| 5,015,240 | 5/1991 | Soproni et al. | 604/192 |
| 5,026,353 | 6/1991 | Bartman | 604/192 |
| 5,032,117 | 7/1991 | Motta | 604/88 |
| 5,084,034 | 1/1992 | Zanotti | 128/762 |
| 5,092,851 | 3/1992 | Ragner | 604/192 |
| 5,092,852 | 3/1992 | Poling | 604/192 |
| 5,097,842 | 3/1992 | Bonn | 128/762 |
| 5,098,401 | 3/1992 | De Lange | 604/192 |
| 5,104,384 | 4/1992 | Parry | 604/192 |
| 5,122,123 | 6/1992 | Vaillancourt | 604/192 |
| 5,135,507 | 8/1992 | Haber et al. | 604/187 |
| 5,282,792 | 2/1994 | Imbert | 604/187 |
| 5,300,038 | 4/1994 | Haber et al. | 604/187 |
| 5,306,258 | 4/1994 | de la Fuente | 604/198 |
| 5,314,503 | 5/1994 | Bobrove et al. | 604/164 |
| 5,460,611 | 10/1995 | Alexander | 604/110 |
| 5,505,721 | 4/1996 | Leach et al. | 128/762 |

*Primary Examiner*—Max Hindenburg
*Attorney, Agent, or Firm*—Roy, Kiesel & Tucker

[57] ABSTRACT

A blood collection system for drawing multiple samples of blood from patients, while minimizing the handling of the blood samples, is provided. The system includes a vial assembly with a coupling which will connect the assembly to the blood flowing from the patient via a connection tube. The vial assembly will also include a storage valve to seal off the assembly; a holder which will have two or more vials, each vial being connected to a supply tube; and a manifold fluidly connecting the coupling to the vial supply tubes. In a particularly preferred embodiment the vial assembly will have a housing with top and bottom sections and the top section will have a cam shutoff for sealing off the vial supply tubes. The system may also include a cannulae assembly which will cover the cannulae needle while the sharp end of the needle is still in the patient.

15 Claims, 2 Drawing Sheets

BLOOD COLLECTION ASSEMBLY WITH PLURALITY OF VIALS

BACKGROUND OF THE INVENTION

1. Field of the Invention

This invention relates, generally, to devices for blood collection, and particularly to devices which are used to collect and store blood prior to testing.

2. Prior Art

Drawing blood for testing is a very common medical procedure. Blood is drawn in both inpatient and outpatient settings. Typically the blood will be drawn for more than one test. From the time the blood is drawn until it is tested, there are several opportunities for the various health-care workers to suffer an injury from a needle stick. Although the piercing from the needle can cause injury in itself, the greater danger is the disease the health care worker may contract from the patient's blood.

The first opportunity for a needle stick when blood is drawn is from the needle which is put into the patient. This needle is known as a cannulae and is typically shorter and thicker than a syringe needle. Although there are safety devices which cover the cannulae after it is removed from the patient, the opportunity for a needle stick still exists during the interval between when the needle is removed from the patient and when the needle is covered or put into a disposal container. Typically, the drawn blood is placed into one or more vials. This can be done using various devices and various methods, but all of these devices and methods require the health care worker to manually fill each vial.

In one configuration the cannulae is connected to a device which looks like a large syringe with a needle protruding into the barrel of the syringe. Vials with piercible tops are placed top down into the barrel so that the needle in the barrel pierces the vial top. The vials have a vacuum so the blood flows into the vial. When one vial is filled the health care worker removes it and places another vial in the barrel, continuing in this fashion until the required number of vials have been filled. The cannulae remains inserted in the patient while the health care worker fills each individual vial, and the movement of the syringe and cannulae will of course present the opportunity to cause pain and vessel damage to the patient.

Although for the apparatus just described the needle inside the syringe barrel is shielded by the barrel, it is nonetheless a needle point which presents another opportunity for a needle stick in the medical waste disposal process. An additional problem with the blood collection process just described is that because the health care worker is trying to fill the individual vials quickly, vial identification may become a problem. It is crucial that blood be correctly identified so as to tie it to the correct patient. Because the needle remains in the patient's arm as the health care worker is filling the vials, the health care worker will fill the vials without taking time to label vials between each filling. Therefore the health care worker must label all the vials either before the filling process or after, and each of these options creates a greater chance for blood misidentification, especially when multiple patients are involved.

In other blood collection systems the cannulae is connected, via intravenous (IV) tubing, to a second needle. This needle is used to penetrate the piercible top of one or more vials. This system is even more dangerous than the syringe system because in this system the needle which pierces the vial tops is more exposed than in the syringe barrel system discussed earlier. Some needles for these types of devices have been manufactured so that the needle is shielded by a cylindrical shield which is just longer than the needle. This shield provides some protection but the contaminated needle point is still accessible. Some needles are equipped with a thin tube-shaped latex cap which is pierced as the needle is inserted into the top of each vial. The latex cap is supposed to move back over the needle when the needle is removed from the vial top. This latex cap provides only minimal protection.

Additionally, the configuration which uses the IV tube and the second needle has the same problem as the syringe barrel configuration discussed earlier in that separate vials are filled and there is an opportunity for misidentification. Some attempts in the art have been made to overcome the multiple vial problem by filling one or two large vials. These large vials can then be poured out into smaller vials (often a full blood-testing profile will need up to six samples) in the lab for testing. This transfer is time-consuming and presents another chance for transmission of infection to a health care worker and another chance for misidentification. In some cases the blood is drawn out of the large vial by piercing the top of the vial with a syringe. When such a syringe is used there is an opportunity for a needle stick and another needle has been used, a needle which must be routed through the medical waste disposal process.

What is needed is a blood collection system which will minimize the number of needles which are used from the first step of drawing the blood from the patient to the final step of a vial of blood being tested in the lab. The system should also minimize the opportunity for needle sticks and should prevent misidentification of samples. Additionally, the system should minimize the number of times blood must be transferred between vials or completely eliminate the need for inter-vial transfers.

OBJECTS OF THE INVENTION

It is an object of the present invention to provide a blood collection system which employs only one needle.

Another object of the present invention is to provide a shielding device on the needle which is used in the patient.

Another object of the present invention is to provide a blood collection system which allows all testing vials to be filled at once.

Another object of the present invention is to provide a blood collection system which minimizes the opportunity for misidentification of blood samples.

SUMMARY OF THE INVENTION

A blood collection system is provided. The system includes a needle assembly which includes a needle with a close-fitting shield. The shield slides forward and locks over the sharp point of the needle while the needle is still in the patient. The system has a vial assembly as well. The vial assembly has a special coupling which routes the blood into two or more vials simultaneously. A tube connects the needle assembly to the vial assembly.

An advantage of the invention is that it employs only a single needle which is used to draw the blood from the patient.

A further advantage of the invention is that the needle used to draw blood from the patient is shielded.

A feature of the invention is that it minimizes the opportunity for misidentification of blood samples.

Another feature of the invention is that when the device is manufactured a vacuum may be placed on several vials in a single step.

These and other objects, advantages, and features of this invention will be apparent from the following descriptions of the invention.

BRIEF DESCRIPTION OF THE DRAWINGS

FIG. 2A shows the sleeve in the position in which the needle is exposed and FIG. 2B shows the sleeve in the position in which the needle is covered.

DETAILED DESCRIPTION OF THE PREFERRED EMBODIMENTS

Figure 1A:
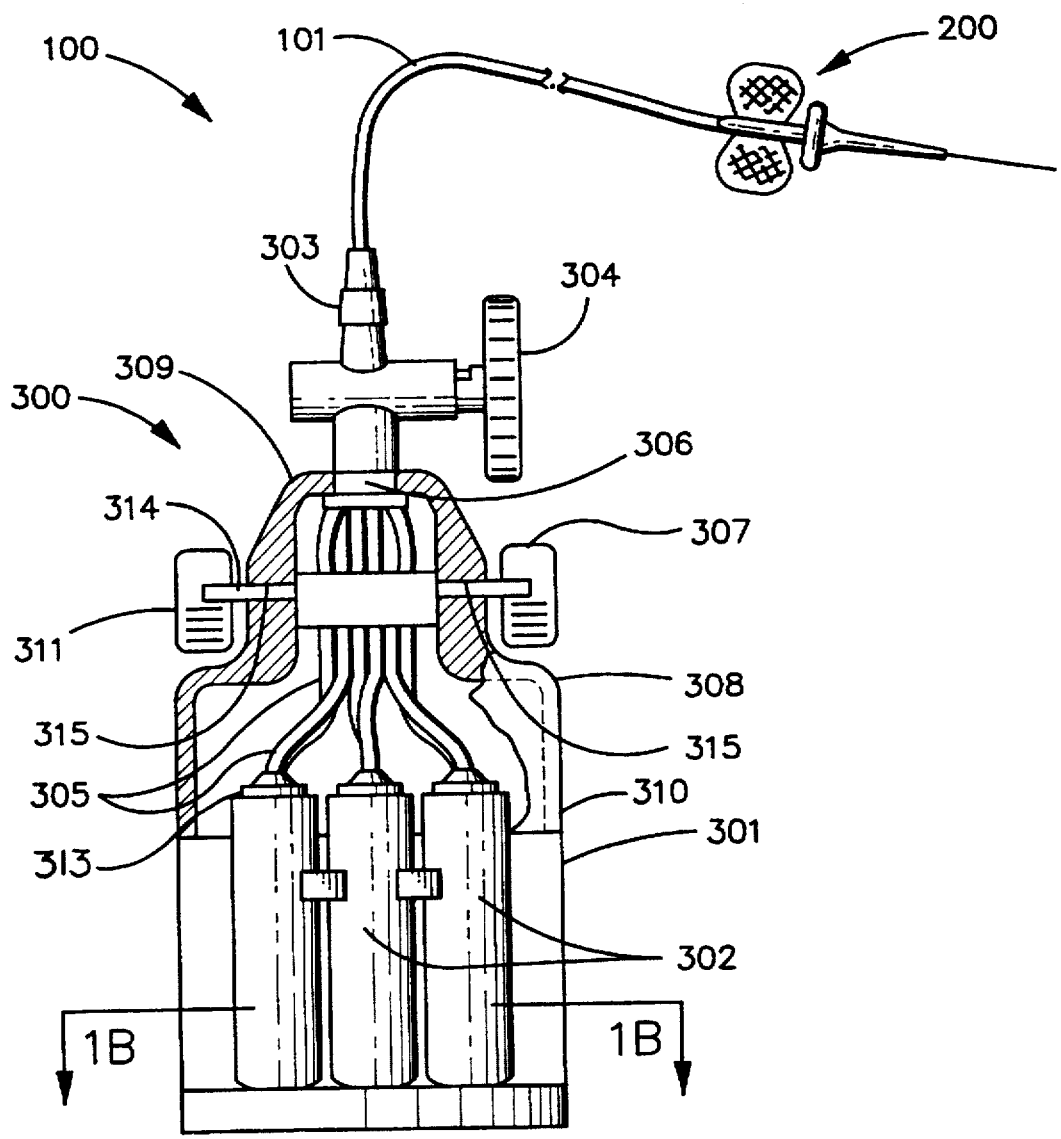
FIG. 1A depicts a preferred embodiment of the vial assembly of the invention. Part of the vial assembly is shown as a sectional view and part is shown as a cutaway view.

Referring to FIG. 1A, the principal parts of blood collection system 100 are cannulae assembly 200, vial assembly 300, and connection tube 101. It is possible that one skilled in the art could use only cannulae assembly 200 of the present invention in conjunction with a different type of vial-filling apparatus, or could use vial assembly 300 in conjunction with a different type of cannulae apparatus. However, in order to obtain the full benefits of the invention it is best if blood collection system 100 is used as a whole.

Vial assembly 300 will now be described with reference to FIG. 1A. Main coupling 303 connects vial assembly 300 to connection tube 101. In the embodiment shown main coupling 303 is a conventional Luer lock which is used to join devices to IV tubing. However, any type of connector which will join connection tube 101 to vial assembly 300 could be used.

Vial assembly 300 includes storage valve means 304. Storage valve means 304 will serve two purposes. Its first purpose will be to help keep a vacuum in vials 302 so that the blood will be drawn into vial assembly 300. The second purpose of storage valve means 304 is to provide an additional means for sealing the blood in vial assembly 300 after the blood has been drawn into vials 302. In the embodiment depicted storage valve means 304 is a simple ball valve which is constructed of PVC but one skilled in the art could use various types of valves for storage valve means 304.

Figure 1B:
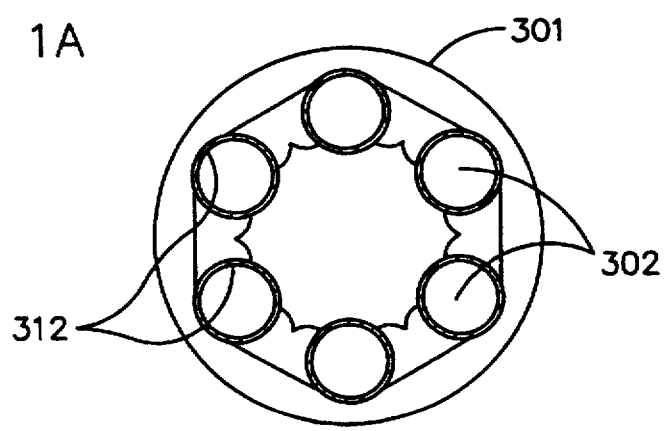
FIG. 1B is a sectional view along view lines 1B as shown in FIG. 1A.

Vial assembly 300 will include two or more vials 302. Vials 302 are usually constructed of glass or PVC or any other material which is capable of maintaining a vacuum. Vials 302 are held in place by vial holder 301. In the embodiment depicted vial holder 301 is a resilient cylindrical member with a bottom and a sidewall with a circular cross-section as shown by FIG. 1B. Vial holder 301 will include vial recesses 312 in which vials 302 are placed. As shown by FIG. 1B vial recesses 312 are shaped so that vials 302 may be snapped into place and held securely within vial holder 301.

The blood will flow from main coupling 303, through storage valve means 304, and through manifold 306. Manifold 306 is designed so that the blood will be routed into vials 302. Manifold 306 is a semi-rigid member manufactured of molded plastic or other materials with similar characteristics to molded plastic. In its simplest embodiment, manifold 306 will be a conical member with one inlet for the blood at one end and a plurality of outlets for the blood at the other end.

Vial supply tubes 305 connect manifold 306 to vials 302. Vial supply tubes 305 may be manufactured of conventional IV tubing. However, it is important that vial supply tubes 305 be manufactured of a material which will not remain pinched off when blood is flowed into vials 302.

Vial supply tube shutoff 307 is set along vial supply tubes 305 between manifold 306 and vials 302. Vial supply tube shutoff 307 will serve two purposes. Its first purpose, like that of storage valve means 304, will be to help keep a vacuum in vials 302 so that the blood will be drawn into vial assembly 300. The second purpose of vial supply tube shutoff 307 is to prevent the flow of blood between vials 302 once the blood has been drawn into vials 302. This may be particularly desirable when different substances have been placed in the vials beforehand as a preparatory step to testing. It will be obvious to one skilled in the art to practice the invention without vial supply tube shutoff 307 if the quality of preventing flow between vials is not necessary.

Vial assembly 300 will also include housing 308 which has top section 309 and bottom section 310. Manifold 306 is fixably attached to top section 309. Bottom section 310 is designed so as to be detachably connected to vial holder 301. The detachable connection will allow the lab personnel to remove housing 308 from vial holder 301 to gain access to vials 302.

Each vial 302 will have top cover 313 which can be removed by lab personnel for testing. Vial supply tubes 305 will be of sufficient length so that the lab personnel can remove housing 308 from vial holder 301 and then remove top covers 313 from vials 302.

FIG. 1A also depicts a preferred embodiment of vial supply tube shutoff 307 which includes shaft 314 which is substantially perpendicular to at least a portion of vial supply tubes 305. For at least part of their length, vial supply tubes 305 are all in the same plane, and shaft 314 is positioned so as to be immediately adjacent to this plane. Shaft 314 is rotatably disposed within shaft apertures 315 in housing 308.

A cam (not shown) is rigidly attached to shaft 314. The cam shaped cam which is sized so that when shaft 314 is rotated the cam will push on vial supply tubes 305 and close them off. Shaft 314 will have at least one handle 311 which may be grasped by hand and used to operate vial supply tube shutoff 307. The cam, shaft 314, and handle 311 will be manufactured of rigid molded plastic or any other suitable material.

The embodiment depicted at FIG. 1B shows six vials 302 arranged in a circular pattern, although one skilled in the art could practice the invention with fewer or more vials 302 and the vials could be arranged in various patterns.

Cannulae assembly 200 will now be described with reference to FIGS. 2A and 2B. In the embodiment depicted cannulae assembly 200 will include needle 201 which has pointed end 209 and fixed end 210. Typically needle 201 will be constructed of steel or another suitable metal. Fixed end 210 is rigidly attached to needle holder 202.

Needle holder 202 will be constructed of molded plastic or other suitable material. Needle holder 202 has needle 201 at one end and cannulae coupling 216 at the other end. Cannulae coupling 216 connects cannulae assembly 200 to connection tube 101. As with main coupling 303 which was described above, cannulae coupling 216 is a conventional Luer lock which is used to join devices to IV tubing. However, any type of connector which will join connection tube 101 to cannulae assembly 200 could be used. In the embodiment shown in FIGS. 2A and 2B, cannulae coupling 216 is positioned within thumb holder 203. Thumb holder 203 is attached to needle holder 202.

Cannulae assembly 200 will also include sleeve 204 which is slidably positionable over needle 201. Sleeve 204 has point-covering end 211, locking end 212, inner surface 214, and outer surface 215. In the embodiment depicted sleeve 204 is constructed of Teflon at point-covering end 211 and of molded plastic at locking end 212; however one skilled in the art could manufacture sleeve 204 of any suitable rigid or semi-rigid material.

Figure 2A:
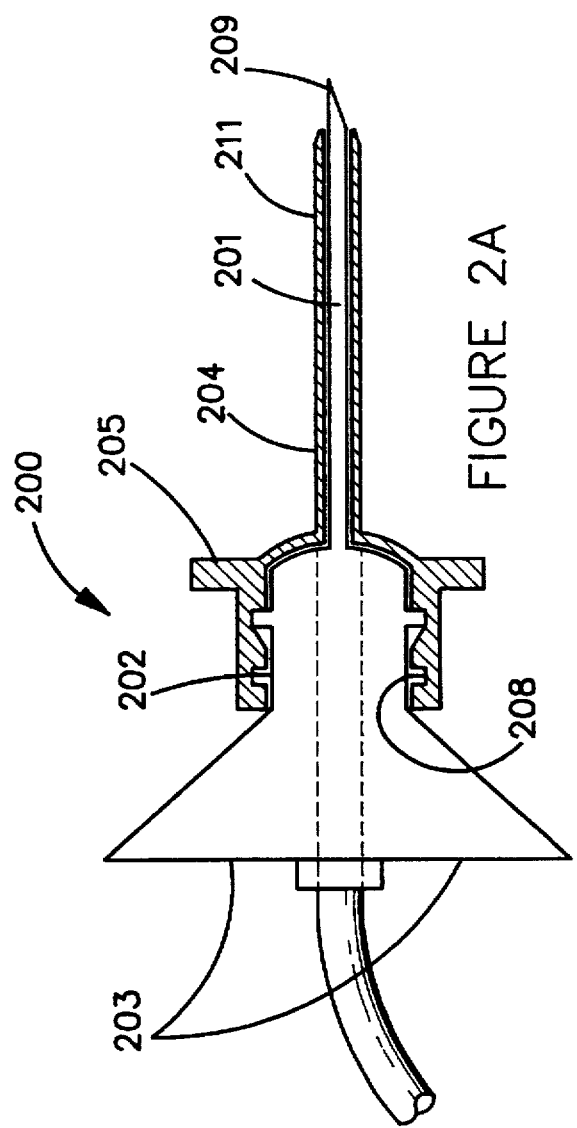
FIGS. 2A and 2B are sectional views of a preferred embodiment of the cannulae assembly of the invention.
Figure 2B:
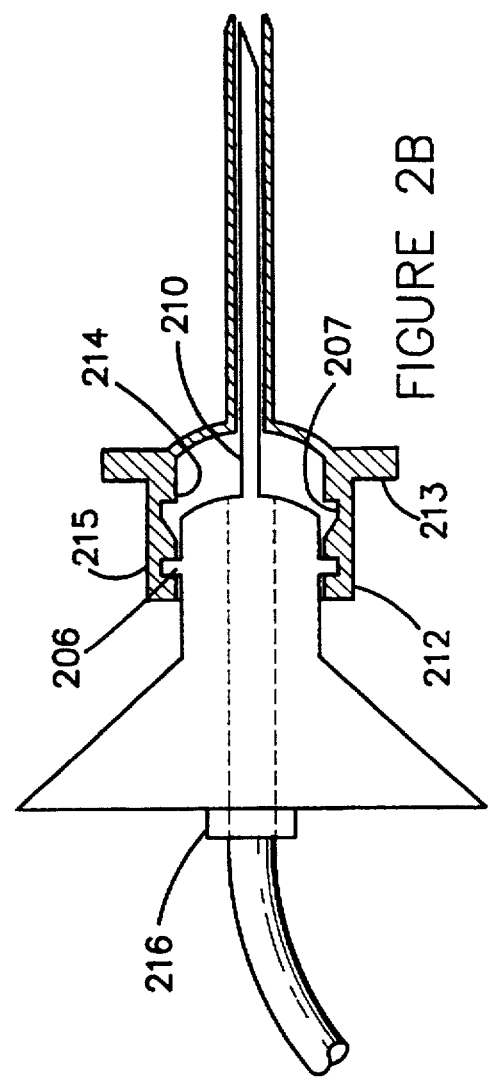

Sleeve 204 is movable from the exposed position depicted in FIG. 2A to the safe position depicted in FIG. 2B. In the exposed position sleeve 204 covers substantially all of needle 201 but leaves a small portion of needle 201 at pointed end 209 exposed. In the safe position sleeve 204 covers all of needle 201 including pointed end 209.

Cannulae assembly 200 will further include push tab 205 which extends radially outward from sleeve outer surface 215 at sleeve locking end 212. Push tab 205 has first surface 213 which is substantially perpendicular to needle 201. First surface protrudes far enough out from sleeve outer surface 215 so that an operator may use his or her finger or fingers to push on first surface 213 and move sleeve 204 from the exposed position to the safe position.

Cannulae assembly 200 will come to the operator with sleeve 204 set in the exposed position. Sleeve inner surface 214 is designed so that sleeve 204 can only be moved from the exposed position to the safe position, and not from the safe position to the exposed position.

This one-way movement feature is accomplished by the use of retention lip 206, exposed position recess 207, and safe position recess 208. Retention lip 206 is rigidly attached to, and extends radially outward from, needle holder 202. Exposed position recess 207 is a cavity in sleeve inner surface 214 which is engaged by retention lip 206 when sleeve 204 is in the exposed position. Exposed position recess 207 is sloped on only one side so that sleeve 204 cannot be pushed toward needle holder to expose needle 201 even further and so that sleeve 204 will be pushed radially outward by retention lip 206 as sleeve 204 is moved to the safe position. FIG. 2A depicts retention lip 206 engaged in exposed position recess 207.

As sleeve 204 is moved into the safe position retention lip 206 will engage safe position recess 208. Unlike exposed position recess 207, safe position recess 208 has no sloped sides so that after retention lip 206 is engaged in safe position recess 208 sleeve 204 cannot be moved out of the safe position.

There are of course other alternate embodiments which are obvious from the foregoing descriptions of the invention, which are intended to be included within the scope of the invention, as defined by the following claims.

I claim:

1. A blood collection vial assembly comprising:
    (1) a main coupling for connecting said vial assembly to a connection tube;
    (2) a storage valve means for sealing off said vial assembly;
    (3) a vial holder having a plurality of vials, each said vial being fluidly connected to a pliable vial supply tube;
    (4) a manifold fluidly connecting said main coupling and said vial supply tubes;
    (5) a housing having a top section and a bottom section, said top section being fixably attached to said manifold, said bottom section being detachably connected to said vial holder; and
    (6) a vial supply tube shutoff for sealing off said vial supply tubes, said vial supply tube shutoff comprising:
        (i) a shaft extending through said housing, said shaft being substantially perpendicular to a portion of said vial supply tubes, said portion of said vial supply tubes being aligned in a plane immediately adjacent to said shaft;
        (ii) two shaft apertures in said housing, said shaft apertures being sized so as to rotatably hold said shaft;
        (iii) a cam disposed in said housing and fixably attached to said shaft, said cam being adapted so that as said shaft is rotated said cam will close off said vial supply tubes; and
        (iv) at least one handle disposed outside of said housing and fixably attached to said shaft.

2. The apparatus in claim 1, wherein said vials are arranged in a circular pattern in said vial holder and said vial assembly further comprises vial recesses which securely hold said vials in said vial holder.

3. A blood collection system comprising:
    (1) a cannulae assembly comprising:
        (i) a needle having a pointed end and a fixed end;
        (ii) a needle holder fixably attached to said fixed end of said needle;
        (iii) a sleeve slidably positionable over said needle, said sleeve having a point-covering end, a locking end, an inner surface, and an outer surface, said sleeve being movable from an exposed position to a safe position, said exposed position being a position wherein said sleeve covers substantially all of said needle leaving only a small portion of said needle at said pointed end exposed, said safe position being a position wherein said sleeve covers all of said needle including said pointed end;
        (iv) a push tab extending radially outward from said sleeve outer surface at said locking end of said sleeve, said push tab having a first surface which is substantially perpendicular to said needle, said first surface being adapted so that an operator may push the sleeve from said exposed position to said safe position by pushing on said first surface with one or more fingers;
        (v) a retention lip fixably attached to said needle holder and extending radially outward from said needle holder;
        (vi) an exposed position recess in said sleeve inner surface at said locking end, said exposed position recess being adapted such that said retention lip may engage said exposed position recess and retain said sleeve in said exposed position; and
        (vii) a safe position recess in said sleeve inner surface at said locking end, said safe position recess being adapted such that said retention lip may engage said safe position recess and retain said sleeve in said safe position;
    (2) a vial assembly comprising:
        (i) a main coupling,
        (ii) a storage valve means for sealing off said vial assembly,
        (iii) a vial holder having a plurality of vials, each said vial being fluidly connected to a vial supply tube,
        (iv) a manifold fluidly connecting said main coupling and said vial supply tubes, and
        (v) a vial supply tube shut-off for sealing off said vial supply tubes; and (3) a connection tube connecting said cannulae assembly and said vial assembly.

4. A blood collection vial assembly comprising:
(1) a main coupling for connecting said vial assembly to a connection tube;
(2) a storage valve means for sealing off said vial assembly;
(3) a vial holder having a plurality of vials, each said vial being fluidly connected to a vial supply tube; and
(4) a manifold fluidly connecting said main coupling and said vial supply tubes.

5. The apparatus in claim 4, further comprising a vial supply tube shutoff for sealing off said vial supply tubes.

6. The apparatus in claim 5,
(1) wherein said blood collection vial assembly further comprises a housing having a top section and a bottom section, said top section being fixably attached to manifold, said bottom section being detachably connected to said vial holder; and
(2) wherein said vial supply tubes are pliable tubes and said vial supply tube shutoff further comprises:
    (i) a shaft extending through said housing, said shaft being substantially perpendicular to a portion of said vial supply tubes, said portion of said vial supply tubes being aligned in a plane immediately adjacent to said shaft,
    (ii) two shaft apertures in said housing, said shaft apertures being sized so as to rotatably hold said shaft,
    (iii) a cam disposed in said housing and fixably attached to said shaft, said cam being adapted so that as said shaft is rotated said cam will close off said vial supply tubes, and
    (iv) at least one handle disposed outside of said housing and fixably attached to said shaft.

7. The apparatus in claim 6, wherein said vials are arranged in a circular pattern in said vial holder and said vial assembly further comprises vial recesses which securely hold said vials in said vial holder.

8. A blood collection system comprising:
(1) a cannulae assembly;
(2) a vial assembly comprising:
    (i) a main coupling,
    (ii) a storage valve means for sealing off said vial assembly,
    (iii) a vial holder having a plurality of vials, each said vial being fluidly connected to a vial supply tube,
    (iv) a manifold fluidly connecting said main coupling and said vial supply tubes, and
    (v) a vial supply tube shut-off for sealing off said vial supply tubes; and
(3) a connection tube connecting said cannulae assembly and said vial assembly.

9. The apparatus in claim 8, wherein said cannulae assembly comprises:
(1) a needle having a pointed end and a fixed end;
(2) a needle holder fixably attached to said fixed end of said needle;
(3) a sleeve slidably positionable over said needle, said sleeve having a point-covering end, a locking end, an inner surface, and an outer surface, said sleeve being movable from an exposed position to a safe position, said exposed position being a position wherein said sleeve covers substantially all of said needle leaving only a small portion of said needle at said pointed end exposed, said safe position being a position wherein said sleeve covers all of said needle including said pointed end;
(4) a push tab extending radially outward from said sleeve outer surface at said locking end of said sleeve, said push tab having a first surface which is substantially perpendicular to said needle, said first surface being adapted so that an operator may push the sleeve from said exposed position to said safe position by pushing on said first surface with one or more fingers;
(5) a retention lip fixably attached to said needle holder and extending radially outward from said needle holder;
(6) an exposed position recess in said sleeve inner surface at said locking end, said exposed position recess being adapted such that said retention lip may engage said exposed position recess and retain said sleeve in said exposed position; and
(7) a safe position recess in said sleeve inner surface at said locking end, said safe position recess being adapted such that said retention lip may engage said safe position recess and retain said sleeve in said safe position.

10. A blood collection vial assembly comprising:
(1) a main coupling for connecting said vial assembly to a connection tube;
(2) a storage valve means for sealing off said vial assembly;
(3) a vial holder having a plurality of vials, each said vial being fluidly connected to a vial supply tube via a needleless connection; and
(4) a manifold fluidly connecting said main coupling and said vial supply tubes.

11. The apparatus in claim 10, further comprising a vial supply tube shutoff for sealing off said vial supply tubes.

12. The apparatus in claim 11,
(1) wherein said blood collection vial assembly further comprises a housing having a top section and a bottom section, said top section being fixably attached to manifold, said bottom section being detachably connected to said vial holder; and
(2) wherein said vial supply tubes are pliable tubes and said vial supply tube shutoff further comprises:
    (i) a shaft extending through said housing, said shaft being substantially perpendicular to a portion of said vial supply tubes, said portion of said vial supply tubes being aligned in a plane immediately adjacent to said shaft,
    (ii) two shaft apertures in said housing, said shaft apertures being sized so as to rotatably hold said shaft,
    (iii) a cam disposed in said housing and fixably attached to said shaft, said cam being adapted so that as said shaft is rotated said cam will close off said vial supply tubes, and
    (iv) at least one handle disposed outside of said housing and fixably attached to said shaft.

13. The apparatus in claim 12, wherein said vials are arranged in a circular pattern in said vial holder and said vial assembly further comprises vial recesses which securely hold said vials in said vial holder.

14. A blood collection system comprising:
(1) a cannulae assembly;
(2) a vial assembly comprising:
    (i) a main coupling, (ii) a storage valve means for sealing off said vial assembly,
(iii) a vial holder having a plurality of vials, each said vial being fluidly connected to a vial supply tube via a needleless connection,
(iv) a manifold fluidly connecting said main coupling and said vial supply tubes, and
(v) a vial supply tube shut-off for sealing off said vial supply tubes; and
(3) a connection tube connecting said cannulae assembly and said vial assembly.

15. The apparatus in claim 14, wherein said cannulae assembly comprises:
(1) a needle having a pointed end and a fixed end;
(2) a needle holder fixably attached to said fixed end of said needle;
(3) a sleeve slidably positionable over said needle, said sleeve having a point-covering end, a locking end, an inner surface, and an outer surface, said sleeve being movable from an exposed position to a safe position, said exposed position being a position wherein said sleeve covers substantially all of said needle leaving only a small portion of said needle at said pointed end exposed, said safe position being a position wherein said sleeve covers all of said needle including said pointed end;
(4) a push tab extending radially outward from said sleeve outer surface at said locking end of said sleeve, said push tab having a first surface which is substantially perpendicular to said needle, said first surface being adapted so that an operator may push the sleeve from said exposed position to said safe position by pushing on said first surface with one or more fingers;
(5) a retention lip fixably attached to said needle holder and extending radially outward from said needle holder;
(6) an exposed position recess in said sleeve inner surface at said locking end, said exposed position recess being adapted such that said retention lip may engage said exposed position recess and retain said sleeve in said exposed position; and
(7) a safe position recess in said sleeve inner surface at said locking end, said safe position recess being adapted such that said retention lip may engage said safe position recess and retain said sleeve in said safe position.

* * * * *